United States Patent [19]

Kerby et al.

[11] Patent Number: 4,965,381
[45] Date of Patent: Oct. 23, 1990

[54] ORGANO-METALLIC CRYSTALLINE POLYMER OF MOLYBDENUM CARBOXYLATE AND BIDENTATE LIGAND

[75] Inventors: Michael C. Kerby, Annandale; Bryan W. Eichhorn, Madison, both of N.J.

[73] Assignee: Exxon Research and Engineering Company, Florham Park, N.J.

[21] Appl. No.: 289,073

[22] Filed: Dec. 22, 1988

[51] Int. Cl.[5] .......................... C07F 9/50; C07F 11/00
[52] U.S. Cl. ......................................... 556/18; 556/63
[58] Field of Search .................................... 556/18, 63

[56] References Cited

PUBLICATIONS

Cotton et al., *Advanced Inorganic Chemistry*, New York; John Wiley & Sons, 1980.

Cotton, *Chem. Soc. Rev.* 4, 27–53 (1975).
Girolami et al., *Inorg. Chem.*, 19, 805–810 (1980).

*Primary Examiner*—Paul F. Shaver
*Attorney, Agent, or Firm*—Jay Simon

[57] ABSTRACT

A novel organo metallic polymer useful as a metathesis catalyst and having the formula

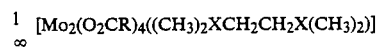

is formed by reacting a carboxylate salt such as dimolybdenum tetra acetate with either tetra methyl ethylene diamine or dimethyl phosphino ethane and crystallizing the polymer.

4 Claims, 1 Drawing Sheet

ORGANO-METALLIC CRYSTALLINE POLYMER OF MOLYBDENUM CARBOXYLATE AND BIDENTATE LIGAND

FIELD OF THE INVENTION

This invention relates to a new organometallic polymer having a highly unsaturated metal-metal bond. The organo-metallic material is crystalline with an infinite repeating pattern in the crystal lattice. More particularly, this invention relates to a new material, useful as a metathesis catalyst, formed by reacting a molybdenum carboxylate complex, e.g., the acetate, with either tetra methyl ethylene diamine (TMED) or dimethyl phosphino ethane (DMPE) to form an infinite array of dimolybdenum tetra acetate units linked by either TMED or DMPE.

BACKGROUND OF THE INVENTION

The insolubility of dimolybdenum tetra acetate in water or organic solvents makes its highly unsaturated metal-metal bond virtually useless in promoting chemical reactions with organic substrates. The chemistry of a related compound, dimolybdenum trifluoro tetra acetate, which is soluble in organic solvents has been studied in relation to the highly unsaturated metal-metal bond.

The newly formed organo metallic polymer of this invention will be useful in metathesis reactions as well as for the oligomerization of alkenes or alkynes. An example of the metathesis reaction known in the literature is the reaction of the unsaturated molybdenum-molybdenum triple bond with an alkyne

More advantageous reactions will come from the new organo metallic material of this invention because of its greater degree of unsaturation, e.g.,

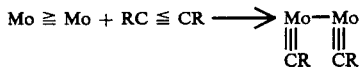

One object of this invention is to provide a raw, more reactive material for carrying out metathesis related, coupling, and oligomerization reactions.

SUMMARY OF THE INVENTION

A new organo-metallic material having the formula $${}^1_\infty [Mo_2(O_2CR)_4((CH_3)_2XCH_2CH_2X(CH_3)_2)]$$

wherein R may be a $C_1$ to $C_5$ alkyl, preferably methyl, and X is either phosphorus or nitrogen, is formed by treating the molybdenum carboxylate, preferably the acetate, neat with a bidentate ligand selected from the group consisting of tetramethyl ethylenediamine and dimethylphosphinoethane, heating the mixture to dissolve the molybdenum carboxylate and cooling the resulting solution to crystallize the organo-metallic polymer.

DETAILED DESCRIPTION OF THE INVENTION

Figure 1:
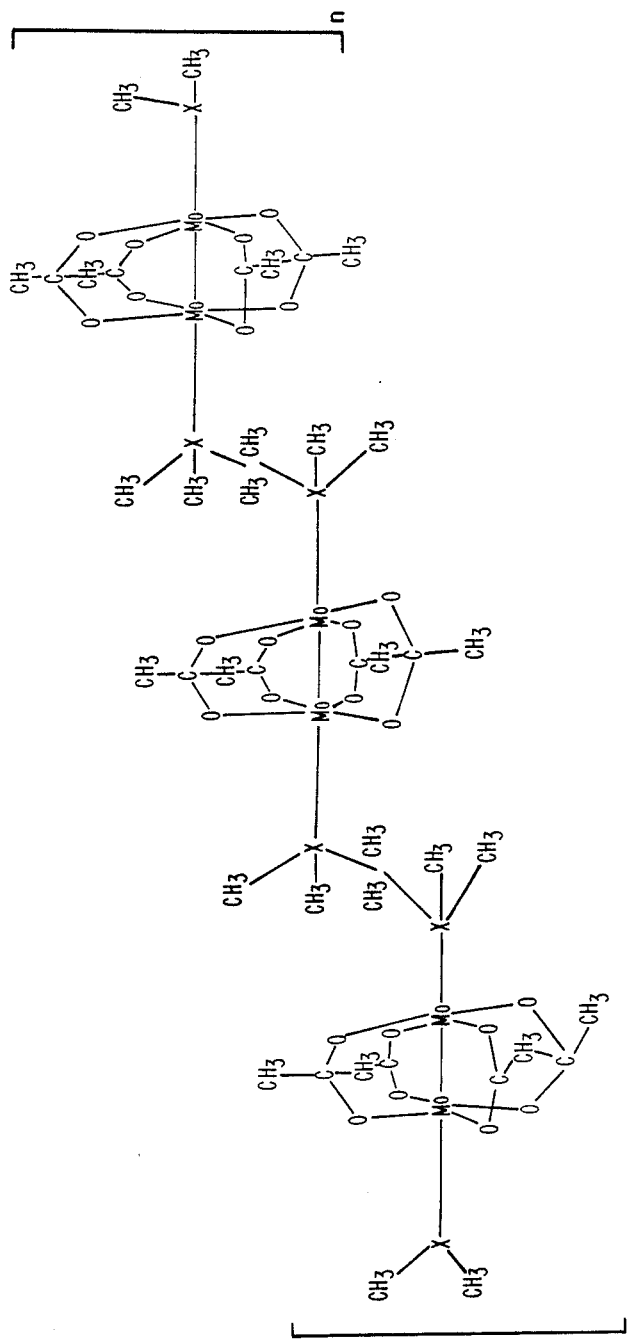
FIG. 1 is representative of a three dimensional arrangement of the new compound illustrated with the dimolybdenum tetraacetate. Preferably, the molybdenum compound is the acetate, although R may be a $C_1$-$C_5$ alkyl group.

The reacting materials are readily available, and the reaction occurs when a large excess of the ligand, used neat, is added to the molybdenum carboxylate complex, and heated above about 100° C. for a period of time sufficient to dissolve the complex in the ligand, usually about 1-3 hours. With the TMED ligand heating at about 100° C. for about one hour is sufficient; for the DMPE ligand, heating at about 130° C. for about 3 hours is sufficient. Higher temperatures can likely be employed, up to ligand decomposition temperatures, but higher temperatures are not believed to provide any advantage.

Reactions pressure is not critical and atmospheric pressure is quite advantageous. The only step of importance is for the complex to enter into solution of the ligand and any temperature or pressure leading to this result is satisfactory.

The reaction occurs in the substantial absence of water, e.g., in a dry box under an argon, or other inert gas.

After dissolving the complex, the reaction mixture is cooled, e.g., by simply removing the heating source, and the organo-metallic material crystallizes during cooling, e.g., to room temperature or to about 30° C. Any excess ligand can be removed by decanting, filtering, or similar means leaving the crystalline organo-metallic compound.

The metathesis process is important commercially in the polymerization of cycloalkanes, and in the SHOP process (Shell Higher Olefins Process), illustrated in *The Organo Metallic Chemistry of the Transition Metals*, Robert H. Crabtree, published by John Wylie & Sons, New York, N.Y., 1988, pp. 264–267, 272–275.

Illustrative of the reactions that can be effected with the organo-metallic polymer are the following:

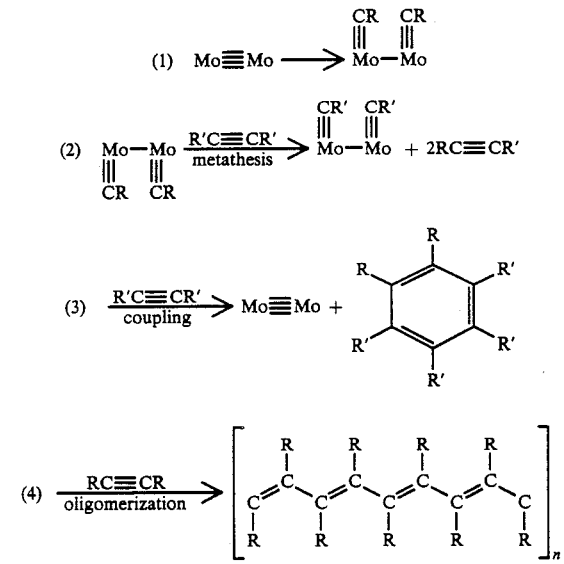

Each of these reactions are effected with an excess of alkyne (R'C≡CR', or RC≡CR), in polar solvents such as lower alcohols, e.g., methanol, ethanol, or water, at moderate reaction temperatures, e.g., 50° C. to 100° C., and atmospheric pressure.

R may be alkyl (i.e., $C_1$–$C_{10}$ preferably $C_1$–$C_5$) or aryl and

R' may be alkyl (i.e., $C_1$–$C_{10}$ preferably $C_1$–$C_5$) or aryl

EXAMPLES

This invention can be illustrated by the following examples.

EXAMPLE 1.

Preparation of

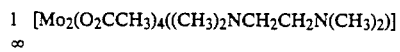

$$\frac{1}{\infty}[Mo_2(O_2CCH_3)_4((CH_3)_2NCH_2CH_2N(CH_3)_2)]$$

(a) To a vial in a dry box under argon was added $Mo_2(O_2CCH_3)_4$ (116 mg, 0.27 mmol) and dry tetramethylethylenediamine (tmed) (10 mL). The mixture was warmed to 100° C. for 1 hour resulting in a clear yellow solution which was slowly cooled to 30° C. After 12 hours somewhat air-stable yellow crystals of the organo-metallic (124 mg, 84% yield) were collected by filtration and dried in vacuo.

(b) Using identical conditions as in (a) with $Mo_2(O_2CCH_3)_4$ (130 mg, 0.30 mmol) and tetramethylethylenediamine (10 mL) organo-metallic collected (133 mg, 81% yield).

IR (cm$^{-1}$, KI) 3010, 2990, 2960, 2870, 2830, 2780, 2660, 2450, 2360, 1617, 1530, 1430, 1345, 1280, 1252, 1165, 1145, 1102, 1037, 1018, 958, 940, 840, 798, 672, 630, 572, 512, 425, 358, 330; Raman (cm$^{-1}$): $\nu_{Mo-Mo}$ 391; MS (CI): 428 (M+ −tmed), 116 (M+ −$Mo_2(O_2CCH_3)_4$).

Analysis calculated for $Mo_2(O_2CCH_3)_4(H_2NCH_2CH_2NH_2)_5$: C, 29.68; H, 7.20; N, 19.23; Mo, 26.34. Found: C, 28.68; H, 6.83; N, 19.13; Mo, 26.57.

Molecular structure of organo-metallic: Selected bond distances: Mo-Mo 2.103 (1), Mo-O 2.128 (2), Mo-N 2.729 (2), N-C 1.470 (3). Selected bond angles (°) O-Mo-Mo 91.0 (1), O-Mo-O 90.7 (1), O-Mo-P 79.9 (1), Mo-Mo-P 170.5 (1), C-P-C 111.9 (2).

EXAMPLE 2

Preparation of

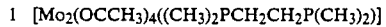

$$\frac{1}{\infty}[Mo_2(OCCH_3)_4((CH_3)_2PCH_2CH_2P(CH_3)_2)]$$

(a) To a vial in a dry box under argon was added $Mo_2(O_2CCH_3)_4$ (53 mg, 0.124 mmol) and dimethylphosphinoethane (2.0 g, 13 mmol, 110 eq) and heated at 130° C. for 2 hours and then cooled to 30° C. The reaction mixture turned from pink to red to purple. After several filtrations to remove undissolved $Mo_2(O_2CCH_3)_4$ (10 mg) light yellow crystals of organo-metallic (5 mg, 9% yield) were collected by filtration and dried in vacuo.

(b) Using identical conditions above with $Mo_2(O_2CCH_3)_4$ (50 mg, 0.117 mmol) and dimethylphosphinoethane (2.0 g, 13 mmol, 110 eq) collected organo-metallic (5 mg, 9% yield).

Molecular structure of organo-metallic. Selected bond distances (Å): Mo-Mo 2.105 (3), Mo-O 2.10 (1), Mo-P 3.064 (4), P-C 1.80 (2). Selected bond angles (°): O-Mo-Mo 92.5 (3), O-Mo-O 89.2 (4), O-Mo-P 91.9 (3), Mo-Mo-P 174.7 (1), C-P-C, 100 (1).

Crystallographic analysis of the organometallics produced in Examples 1 and 2 showed that the bidentate ligands (TMED, DMPE) produced a zig-zig conformation comprised of infinitely repeating $Mo_2 (O_2CCH_3)_4$ units.

What is claimed is:

1. 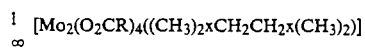

$$\frac{1}{\infty}[Mo_2(O_2CR)_4((CH_3)_2xCH_2CH_2x(CH_3)_2)]$$

wherein

R is $C_1$–$C_5$ alkyl, and x is phosphorus or nitrogen

2. 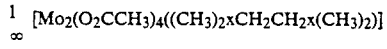

$$\frac{1}{\infty}[Mo_2(O_2CCH_3)_4((CH_3)_2xCH_2CH_2x(CH_3)_2)]$$

wherein

X is phosphorus or nitrogen

3. The composition of claim 2 wherein x is phosphorus.

4. The composition of claim 2 wherein x is nitrogen.

* * * * *